United States Patent [19]
Chenard

[11] Patent Number: 6,124,361
[45] Date of Patent: Sep. 26, 2000

[54] BICYCLO[3.1.0]HEXANES AND RELATED COMPOUNDS

[75] Inventor: Bertrand L. Chenard, Waterford, Conn.

[73] Assignee: Pfizer Inc, New York, N.Y.

[21] Appl. No.: 09/222,600

[22] Filed: Dec. 29, 1998

Related U.S. Application Data

[60] Provisional application No. 60/070,171, Dec. 31, 1997, and provisional application No. 60/070,759, Jan. 8, 1998.

[51] Int. Cl.⁷ .......................... A61K 31/194; C07C 61/13
[52] U.S. Cl. .......................... 514/561; 514/357; 514/438; 514/428; 514/317; 514/566; 546/335; 546/276.4; 546/205; 549/79
[58] Field of Search ............................. 562/501; 514/561, 514/566

[56] References Cited

U.S. PATENT DOCUMENTS 5,661,184  8/1997  Helton et al. ........................... 514/574

FOREIGN PATENT DOCUMENTS 751117  1/1997  European Pat. Off. .

*Primary Examiner*—Jane Fan
*Attorney, Agent, or Firm*—Peter C. Richardson; P. H. Ginsburg

[57] ABSTRACT

The present invention relates to compounds of the formula I, as defined in the specification, pharmaceutical compositions containing such compounds the use of such compounds to treat neurological and psychiatric disorders.

11 Claims, No Drawings

BICYCLO[3.1.0]HEXANES AND RELATED COMPOUNDS

This Application claims the benefit of U.S. Provisional Application No. 60/070,171, filed Dec. 31, 1997, and of U.S. Provisional Application No. 60/070,759, filed Jan. 8, 1998.

BACKGROUND OF THE INVENTION

The present invention relates to compounds of the formula 1, as described below, their pharmaceutically acceptable salts, pharmaceutical compositions containing them and their use in treating neurological and psychiatric disorders.

The role of excitatory amino acids, such as glutamic acid and aspartic acid, as the predominant mediators of excitatory synaptic transmission in the central nervous system has been well established. Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). These amino acids function in synaptic transmission primarily through excitatory amino acid receptors. These amino acids also participate in a variety of other physiological processes such as motor control, respiration, cardiovascular regulation, sensory perception, and cognition.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA). The second general type is the G-protein or second messenger-linked "metabotropic" excitatory amino acid receptor. This second type, when activated by the agonists quisqualate, ibotenate, or trans-1-aminocyclopentane-1,3-dicarboxylic acid, leads to enhanced phosphoinositide hydrolysis in the postsynaptic cell. Both types of receptors appear not only to mediate normal synaptic transmission along excitatory pathways, but also participate in the modification of synaptic connection during development and changes in the efficiency of synaptic transmission throughout life. Schoepp, Bockaert, and Sladeczek. *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

Excitatory amino acid excitotoxicity has been implicated in the pathophysiology of a number of neurological disorders. This excitotoxicity has been implicated in the pathophysiology of acute and chronic neurodegenerative conditions including stroke, cerebral ischemia, spinal cord trauma, head trauma, Alzheimer's Disease, Huntington's Chorea, amyotrophic lateral sclerosis, epilepsy, AIDS-induced dementia, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, ocular damage and retinopathy, idiopathic and drug-induced Parkinson's Disease and cerebral deficits subsequent to cardiac bypass surgery and grafting. Other neurological conditions that are caused by glutamate dysfunction require neuromodulation. These other neurological conditions include muscular spasms, migraine headaches, urinary incontinence, psychosis, addiction withdrawal (such as alcoholism and drug addiction including opiate, cocaine and nicotine addiction), opiate tolerance, anxiety, emesis, brain edema, chronic and acute pain, convulsions, retinal neuropathy, tinnitus and tardive dyskinesia. The use of a neuroprotective agent, such as an AMPA receptor antagonist, is believed to be useful in treating these disorders and/or reducing the amount of neurological damage associated with these disorders. The excitatory amino acid receptor (EAA) antagonists are also believed to be useful as analgesic agents.

The metabotropic glutamate receptors are a highly heterogeneous family of glutamate receptors that are linked to multiple second-messenger pathways. Generally, these receptors function to modulate the presynaptic release of glutamate, and the postsynaptic sensitivity of the neuronal cell to glutamate excitation. The metabotropic glutamate receptors (mGluR) have been pharmacologically divided into two subtypes. One group of receptors ("Class I receptors") is positively coupled to phospholipase C, which causes hydrolysis of cellular phosphoinositides (PI). This first group are termed PI-linked metabotropic glutamate receptors. The second group of receptors ("Class II receptors") is negatively coupled to adenyl cyclase, which prevents the forskolin-stimulated accumulation of cyclic adenosine monophosphate (cAMP). Schoepp and Conn, *Trends Pharmacol. Sci.*, 14, 13 (1993). Receptors within this second group are termed cAMP-linked metabotropic glutamate receptors. Agonists of the cAMP-linked metabotropic glutamate receptors should be useful for the treatment of acute and chronic neurological conditions and psychiatric conditions.

Compounds have recently been discovered that effect metabotropic glutamate receptors, but have no effect on ionotropic glutamate receptors. (1S,3R)-1-Aminocyclopentane-1,3-dicarboxylic acid (1S,3R-ACPD) is an agonist of PI-linked and cAMP-linked metabotropic glutamate receptors. Schoepp, Johnson, True, and Monn., *Eur. J. Pharmacol.*, 207, 351 (1991); Schoepp, Johnson, and Monn, *J. Neurochem.*, 58, 1184 (1992). (2S,3S,4S)-2-(carboxycyclopropyl) glycine (L-CCG-1) was recently described as a selective cAMP-linked metabotropic glutamate receptor agonist: however, at higher concentrations, this compound has activity at PI-linked metabotropic receptors. Nakagawa, et al., *Eur J. Pharmacol.*, 184, 205 (1990): Hayashi, et al., *Br. J. Pharmacol.*, 197, 539 (1992): Schoepp et al., *J. Neurochem.*, 63., 769–772 (1994).

European Patent Application EP 696577AI, which was published on Feb. 14, 1996, refers to certain synthetic amino acids that are described as being selective for the negatively coupled cAMP linked metabotropic glutamate receptors (i.e., Class II metabotropic glutamate receptors).

The compounds of formula I and their pharmaceutically acceptable salts are metabotropic glutamate receptor ligands that are selective for Class II metabotropic glutamate receptors.

SUMMARY OF THE INVENTION

This invention relates to compounds of the formula

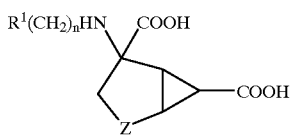

I wherein n is 0–6;

Z is ($C_1$–$C_4$) alkylene, oxygen, sulfur, NH or N($C_1$–$C_6$) alkyl;

$R^1$ is hydrogen, ($C_1$–$C_6$)alkyl, aryl or heteroaryl, wherein said aryl is selected from phenyl and naphthyl and said heteroaryl is selected from 5 and 6 membered aromatic heterocyclic rings that contain from one to four heteroatoms selected, independently, from nitrogen, oxygen and sulfur, and wherein said aryl and heteraryl moieties can optionally be substituted with one or more substituents, preferably with one or two substituents, that are selected, independently, from halo (es, fluoro, chloro, bromo or iodo), —SO($C_1$–$C_6$)alkyl, —$SO_2R^4$, —$SO_2NR^5R^6$, ($C_1$–$C_6$)alkyl optionally substituted with from one to seven fluorine atoms, ($C_1$–$C_6$)alkoxy optionally substituted with from one to seven fluorine atoms, amino, nitro, cyano, carboxy, —$CO_2$($C_1$–$C_6$) alkyl, ($C_1$–$C_6$)alkylamino, di-[($C_1$–$C_6$)alkyl]amino phenoxy, anilino and phenylthio;

$R^4$ is —O($C_1$–$C_6$)alkyl, ($C_1$–$C_6$)alkyl or phenyl; and $R^5$ and $R^6$ are independently selected from hydrogen, ($C_1$–$C_6$)alkyl and phenyl;

with the proviso that $R^1$ can not be hydrogen when n is zero, and with the proviso that none of the foregoing heteroaryl moieties may contain more than one ring oxygen atom or more than one ring sulfur atom;

and the pharmaceutically acceptable salts of such compounds.

Examples of the heteroaryl moieties of said heteroaryl-($C_0$–$C_6$)alkyl are the following: oxazolyl, isoxazoyl, thiazolyl, isothiazolyl, furanyl, pyrazolyl, pyrrolyl, tetrazolyl, triazolyl, thienyl, imidazolyl, pyridinyl, and pyrimidinyl.

This invention also relates to compounds of the formula

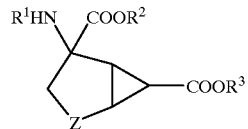

II wherein $R^1$ and Z are defined as for formula I above and $R^2$ and $R^3$ are selected, independently, from hydrogen and ($C_1$–$C_6$)alkyl, with the proviso that only one of $R^2$ and $R^3$ can be hydrogen.

Compounds of the formula II are intermediates in the synthesis of compounds of the formula I.

Preferred compounds of the formula I include those wherein $R^1$ is a pyrid-3-yl or pyrid-4-yl group.

Other examples of preferred compounds of the formula I are those wherein $R^1$ is linked to the bicyclic ring depicted in structural formula I via an alkyl group.

Other examples of preferred compounds of the formula I are those wherein $R^1$ is a mono- or disubstituted phenyl group wherein one of the substituents is in the para position.

Other examples of preferred compounds of the formula I are those wherein Z is $CH_2$.

Other examples of preferred compounds of the formula I are those wherein $R^1$ is a thien-2-ylmethyl group.

The compounds of formula I and their pharmaceutically acceptable salts are metabotropic glutamate receptor ligands and are useful in the treatment of a variety of neurological and psychiatric disorders. Examples of neurological disorders that can be treated with the compounds of formula I and their pharamaceutically acceptable salts are cerebral deficits subsequent to cardiac bypass surgery and grafting, cerebral ischemia (e.g., stroke and cardiac arrest), spinal cord trauma, head trauma, Alzheimer's Disease, Huntington's disease, amyotrophic lateral sclerosis, AIDS-induced dementia, muscular spasms, migrane headache, urinary incontinence, convulsions, perinatal hypoxia, hypoglycemic neuronal damage, chemical dependencies and addictions (e.g., a dependency on, or addiction to opiates, benzodiazepines, cocaine, nicotine or ethanol), drug or alcohol withdrawal symptoms, ocular damage and retinopathy, cognitive disorders, idiopathic and drug-induced Parkinson's Disease, emesis, brain edema, acute or chronic pain, sleep disorders, Tourette's syndrome, attention deficit disorder and tardive dyskinesia. Examples of psychiatric disorders that can be treated with the compounds of formula I and their pharamaceutically acceptable salts are schizophrenia, anxiety and related disorders (e.g., panic attack and stress-related disorders), depression, bipolar disorders, psychosis, and obsessive compulsive disorders.

Examples of specific preferred compounds of the formula I are those wherein Z is $CH_2$ and $R^1$ is one of the following groups.

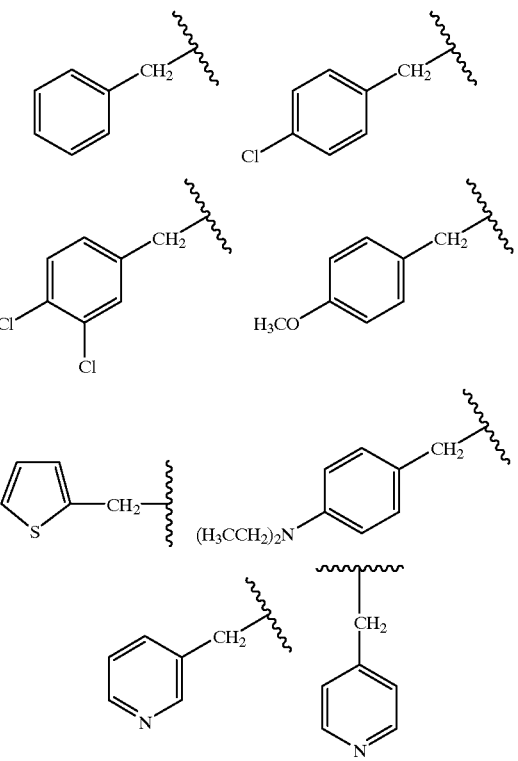

Another example of a specific preferred compound of the formula I is the compound of formula I wherein Z is $CH_2$ and $R^1$ is 3-methylbutyl.

Other examples of specific compounds of the formula I are the following:

2-Benzylamino-bicyclo[3.1.0]hexane-2,6-dicarboxylic acid;

2-(4-Methoxy-benzylamino)-bicyclo[3.1.0]hexane-2,6-dicarboxylic acid;

2-(4-Diethylamino-benzylamino)-bicyclo[3.1.0]hexane-2,6-dicarboxylic acid;

2-(4-Chloro-benzylamino)-bicyclo[3.1.0]hexane-2,6-dicarboxylic acid;

2-(3,4-Dichloro-benzylamino)-bicyclo[3.1.0]hexane-2,6-dicarboxylic acid;

2-[(Pyridin-3-ylmethyl)-amino]-bicyclo[3.1.0]hexane-2,6-dicarboxylic acid;

2-[(Pyridin-4-ylmethyl)-amino]-bicyclo[3.1.0]hexane-2,6-dicarboxylic acid;

2-[(Thiophen-2-ylmethyl)-amino]-bicyclo[3.1.0]hexane-2,6-dicarboxylic acid;

2-(4-Pyrrolidin-1-yl-benzylamino)-bicyclo[3.1.0]hexane-2,6-dicarboxylic acid;

2-(4-Piperidin-1-yl-benzylamino)-bicyclo[3.1.0]hexane-2,6-dicarboxylic acid and

2-[(6-Pyrrolidin-1-yl-pyridin-3-ylmethyl)-amino]-bicyclo[3.1.0]hexane-2,6-dicarboxylic acid.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The present invention also relates to the pharmaceutically acceptable base addition salts of compounds of the formula I. These salts are all prepared by conventional techniques. The chemical bases that are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc.

This invention also relates to a pharmaceutical composition for treating a disorder or condition, the treatment or prevention of which can be effected or facilitated by modulating (i.e., increasing or decreasing) glutamate neurotransmission in a mammal, comprising an amount of a compound of the formula I, or a pharmaceutically effective salt thereof, that is effective in treating such disorder or condition and a pharmaceutically acceptable carrier.

This invention also relates to a method of treating a disorder or condition, the treatment of which can be effected or facilitated by modulating glutamate neurotransmission in a mammal, comprising administering to a mammal in need of such treatment an amount of a compound of the formula I, or a pharmaceutically effective salt thereof, that is effective in treating such disorder or condition.

This invention also relates to a pharmaceutical composition for treating a condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, chemical dependencies and addictions (e.g., addictions to or dependencies on alcohol, opiates, benzodiazepines, nicotine, heroin or cocaine), ocular damage, retinopathy, retinal neuropathy, tinnitus, idiopathic and drug induced Parkinson's Disease, anxiety, panic disorder, schizophienia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting in a mammal, comprising a glutamate neurotransmission modulating effective amount of a compound of the formula I, or a pharmaceutically salt thereof, and a pharmaceutically acceptable carrier.

This invention also relates to a method for treating a condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, chemical dependencies and addictions (e.g., addictions to or dependencies on alcohol, opiates, benzodiazepines, nicotine, heroin or cocaine), ocular damage, retinopathy, retinal neuropathy, tinnitus, idiopathic and drug induced Parkinson's Disease, anxiety, panic disorder, schizophienia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting in a mammal, comprising administering to a mammal requiring such treatment a glutamate neurotransmission modulating effective amount of a compound of the formula I, or a pharmaceutically acceptable salt thereof.

This invention also relates to a pharmaceutical composition for treating a disorder or condition, the treatment of which can be effected or facilitated by modulating glutamate neurotransmission in a mammal, comprising a glutamate neurotransmission modulating effective amount of a compound of the formula I, or a pharmaceutically acceptable salt thereof, and a pharmaceutically acceptable carrier.

This invention also relates to a method for treating a disorder or condition, the treatment of which can be effected or facilitated by modulating glutamate neurotransmission in a mammal, comprising administering to a mammal requiring such treatment a glutamate neurotransmission modulating effective amount of a compound of the formula I or a pharmaceutically acceptable salt thereof.

This invention also relates to a method of treating a condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, chemical dependencies and addictions (e.g., addictions to or dependencies on alcohol, opiates, benzodiazepines, nicotine, heroin or cocdine), ocular damage, retinopathy, retinal neuropathy, tinnitus, idiopathic and drug induced Parkinson's Disease, anxiety, panic disorder schizophienia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting in a mammal, comprising administering to a mammal in need of such treatment an amount of a compound of the formula I that is effective in treating such condition.

This invention also relates to a pharmaceutical composition for treating a condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, chemical dependencies and addictions (e.g., addictions to or dependencies on alcohol, opiates, benzodiazepines, nicotine, heroin or cocaine), ocular damage, retinopathy, retinal neuropathy, tinnitus, idiopathic and drug induced Parkinson's Disease, anxiety, panic disorder, schizophienia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting in a mammal, comprising an amount of a compound of the formula I that is effective in treating such condition and a pharmaceutically acceptable carrier.

This invention also relates to a method for treating a disorder or condition, the treatment of which can effected or facilitated by modulating glutamate neurotransmission in a mammal, comprising administering to a mammal requiring such treatment:

(a) a compound of the formula I, or a pharmaceutically acceptable salt thereof; and (b) a serotonin reuptake inhibitor (e.g., sertraline, fluoxetine, fluvoxamine, etc.) or a serotonin-1A ($5HT_{1A}$) receptor ligand (e.g., buspirone, flesinoxan, etc.) or a pharmaceutically acceptable salt of such inhibitor or ligand;
wherein the amounts of the compound of formula I and the serotonin reuptake inhibitor or $5HT_{1A}$ receptor ligand that are employed in such method are such that the combination of the two active ingredients is effective in treating such disorder or condition.

This invention also relates to a pharmaceutical composition for treating a disorder or condition, the treatment of which can effected or facilitated by modulating glutamate neurotransmission in a mammal, comprising:

(a) a compound of the formula I, or a pharmaceutically acceptable salt thereof;

(b) a serotonin reuptake inhibitor (e.g., sertraline, fluoxetine, fluvoxamine, etc.) or a serotoin-1A ($5HT_{1A}$) receptor ligand (e.g., buspirone, flesinoxan, etc.) or a pharmaceutically acceptable salt of such inhibitor or ligand; and (c) a pharmaceutically acceptable carrier;
wherein the amounts of the compound of formula I and the serotonin reuptake inhibitor or $5HT_{1A}$ receptor ligand that are contained in such compostion are such that the combination of the two active ingredients is effective in treating such disorder or condition.

This invention also relates to a method for treating a disorder or condition, the treatment of which can effected or facilitated by modulating glutamate neurotransmission in a mammal, comprising administering to a mammal requiring such treatment:

(a) a glutamate neurotransmission modulating compound, or a pharmaceutically acceptable salt thereof; and (b) a serotonin reuptake inhibitor (e.g., sertraline, fluoxetine, fluvoxamine, etc.) or a serotonin-1A ($5HT_{1A}$) receptor ligand (e.g., buspirone, flesinoxan, etc.) or a pharmaceutically acceptable salt of such inhibitor or ligand;
wherein the amounts of the glutamate neurotransmission modulating compound and the serotonin reuptake inhibitor or $5HT_{1A}$ receptor ligand that are employed in such method are such that the combination of the two active ingredients is effective in treating such disorder or condition.

This invention also relates to a pharmaceutical composition for treating a disorder or condition, the treatment of which can effected or facilitated by modulating glutamate neurotransmission in a mammal, comprising:

(a) a glutamate neurotransmission modulating compound or a pharmaceutically acceptable salt thereof;

(b) a serotonin reuptake inhibitor (e.g., sertraline, fluoxetine, fluvoxamine, etc.) or a serotoin-1A ($5HT_{1A}$) receptor ligand (e.g., buspirone, flesinoxan, etc.) or a pharmaceutically acceptable salt of such inhibitor or ligand; and (c) a pharmaceutically acceptable carrier;
wherein the amounts of the glutamate neurotransmission modulating compound and the serotonin reuptake inhibitor or $5HT_{1A}$ receptor ligand that are contained in such compostion are such that the combination of the two active ingredients is effective in treating such disorder or condition.

This invention also relates to a method for treating a disorder or condition, selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, chemical dependencies and addictions (e.g., addictions to or dependencies on alcohol, opiates, benzodiazepines, nicotine, heroin or cocaine), ocular damage, retinopathy, retinal neuropathy, tinnitus, idiopathic and drug induced Parkinson's Disease, anxiety, panic disorder, schizophienia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting in a mammal, comprising administering to a mammal requiring such treatment:

(a) a compound of the formula I, or a pharmaceutically acceptable salt thereof; and (b) a serotonin reuptake inhibitor (e.g., sertraline, fluoxetine, fluvoxamine, etc.) or a serotonin-1A ($5HT_{1A}$) receptor ligand (e.g., buspirone, flesinoxan, etc.) or a pharmaceutically acceptable salt of such inhibitor or ligand;
wherein the amounts of the compound of formula I and the serotonin reuptake inhibitor or $5HT_{1A}$ receptor ligand that are employed in such method are such that the combination of the two active ingredients is effective in treating such disorder or condition.

This invention also relates to a pharmaceutical composition for treating a disorder or condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, chemical dependencies and addictions (e.g., addictions to or dependencies on alcohol, opiates, benzodiazepines, nicotine, heroin or cocaine), ocular damage, retinopathy, retinal neuropathy, tinnitus, idiopathic and drug induced Parkinson's Disease, anxiety, panic disorder, schizophienia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting in a mammal, comprising:

(a) a compound of the formula I, or a pharmaceutically acceptable salt thereof; and (b) a serotonin reuptake inhibitor (e.g., sertraline, fluoxetine, fluvoxamine, etc.) or a serotoin-1A (5HT$_{1A}$) receptor ligand (e.g., buspirone, flesinoxan, etc.) or a pharmaceutically acceptable salt of such inhibitor or ligand; and (c) a pharmaceutically acceptable carrier;
wherein the amounts of the compound of formula I and the serotonin reuptake inhibitor or 5HT$_{1A}$ receptor ligand that are contained in such composition are such that the combination of the two active ingredients is effective in treating such disorder or condition.

Unless otherwise indicated, the alkyl groups referred to herein, as well as the alkyl moieties of other groups referred to herein (e.g., alkoxy), may be linear or branched, and they may also be cyclic (e.g., cyclopropyl, cyclobutyl, cyclopentyl, or cyclohexyl) or be linear or branched and contain cyclic moieties.

The term "treating" as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

Unless otherwise indicated, "halo" and "halogen", as used herein, refer to fluorine, bromine, chlorine or iodine.

Compounds of the formula I may have chiral centers and therefore may exist in different enantiomeric and diastereomic forms. This invention relates to all optical isomers and all other stereoisomers of compounds of the formula I, and to all racemic and other mixtures thereof, and to all pharmaceutical compositions and methods of treatment defined above that contain or employ such isomers or mixtures.

Formula I above includes compounds identical to those depicted but for the fact that one or more hydrogen or carbon atoms are replaced by isotopes thereof. Such compounds are useful as research and diagnostic tools in metabolism pharmokinetic studies and in binding assays. Specific applications in research include radioligand binding assays, autoradiography studies and in vivo binding studies.

DETAILED DESCRIPTION OF THE INVENTION

The compounds of formula I can be prepared according to the methods of Scheme 1. In the reaction Scheme and discussion that follow, unless otherwise indicated, n, Z, R$^1$, R$^2$, R$^3$ R$^4$, R$^5$ and R$^6$ and structural formulas I and II are defined as above.

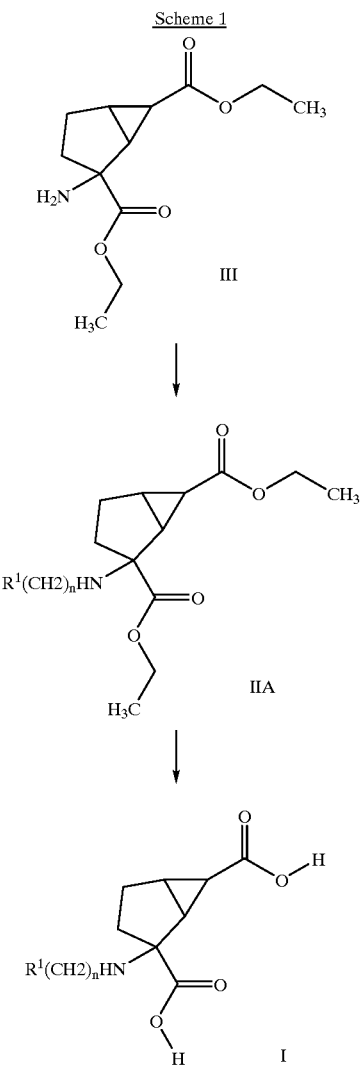

Scheme 2

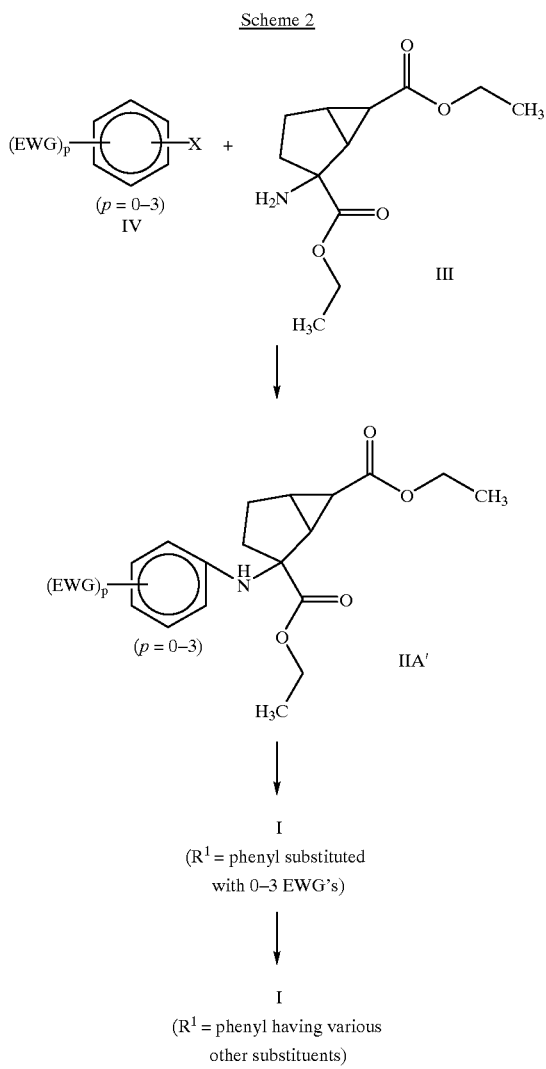

(R¹ = phenyl substituted with 0–3 EWG's)

I
(R¹ = phenyl having various other substituents)

Scheme 3

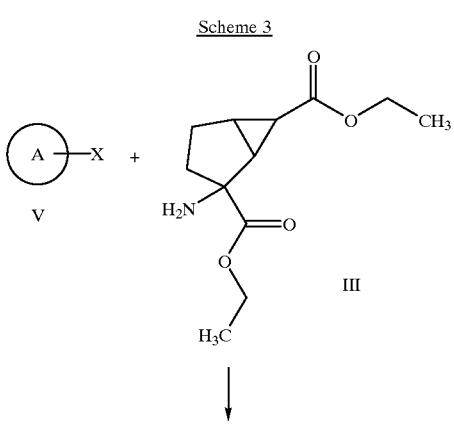

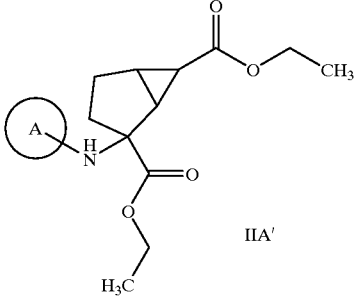

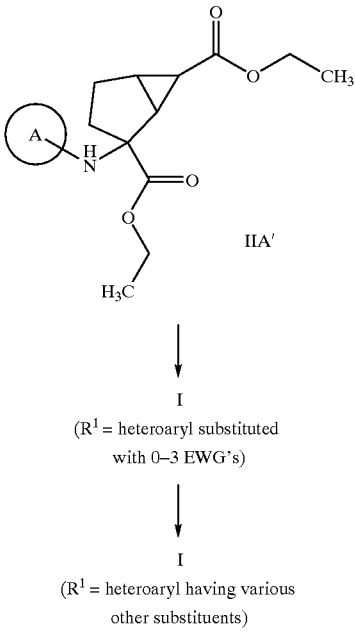

(R¹ = heteroaryl substituted with 0–3 EWG's)

I
(R¹ = heteroaryl having various other substituents)

Scheme 1 illustrates the preparation of all compounds of the formula I in which there is an alkyl linkage of $R^1$ to the amino nitrogen of formula I.

Referring to Scheme I, a compound of the formula III is reacted with the appropriate aldehyde of the formula $R^1(CH_2)_m CHO$, wherein m is equal to n−1, to form a compound of the formula IIA.

The above reductive amination reaction can be carried out using standard methods well known to those of skill in the art. This reaction is typically carried out in the presence of a reducing agent such as sodium cyanoborohydride, sodium triacetoxyborohydride, sodium borohydride, hydrogen (or a chemical hydrogen source such as formic acid or ammonium formate) and a metal catalyst such as platinum, palladium or rhodium, zinc and hydrochloric acid, borane dimethylsulfide or formic acid, at a temperature from about −60° C. to about 50° C. Suitable reaction inert solvents for this reaction include lower alcohols (e.g., methanol, ethanol and isopropanol), dioxane, methylene chloride, dichloroethane, acetic acid and tetrahydrofuran (THF). Preferably, the solvent is methylene chloride or dichloroethane, the temperature is about 25° C., and the reducing agent is sodium triacetoxyborohydride.

The compounds of formula IIA formed in the above reaction can be converted onto the corresponding desired compounds of the formula I by subjecting them to acid or base hydrolysis, using methods well known to those of skill in the art. Suitable acids for the use in acid hydrolysis compound of the formula IIA include mineral acids such as hydrofluoric acid, sulfuric acid, hydrochloric acid and hydrobromic acid. Suitable bases for use in base hydrolysis of compounds of the formula IIA include alkali metal hydroxides and barium hydroxide. The reaction temperature for the acid and base hydrolysis reactions can range from about 0° C. to about 100° C. Preferably, these reactions are carried out at about the reflux temperature of the reaction mixture.

Compounds of the formula I, wherein $R^1$ is aryl or heteroaryl and n is zero can be formed from the corresponding compounds of the formula IIA, as illustrated in Schemes 2 and 3, respectively. Compounds of the formula IIA wherein $R^1$ is aryl can be formed, as illustrated in Scheme 2, by reacting the corresponding compounds of the formula III, as depicted in Scheme 2, with a compound of the formula $R^1X$, wherein X is a leaving group such as halo, triflate, mesylate or tosylate. This reaction is generally carried out in a solvent such as ethanol, N,N-dimethylformamide (DMF), N,N-dimethylacetamide, acetonitrile, nitromethene, dioxane or dichloroethane, preferably DMF, at a temperature from about 0° C. to about 160° C., preferably at about the reflux temperature. Scheme 2 specifically depicts the synthesis of compounds of the formula I wherein $R^1$ is an unsubstituted phenyl group or a phenyl group having from 0 to 3 electron withdrawing groups (EWG'S) as substituents. Examples of EWG's include, but are not limited to, nitro, $(C_1-C_6)$alkyl-SO—, $(C_1-C_6)$alkyl-SO$_2$—, $(C_1-C_6)$alkyl-O—C(=O)—, $[(C_1-C_6)$alkyl$)]_2$NC(=O)—, cyano, —SO$_2R^4$ and SO$_2$NR$^5R^6$.

In an analogous fashion, compounds of the formula I wherein $R^1$ is heteroaryl and n is zero may be prepared as illustrated in Scheme 3. Referring to Scheme 3, a compound of the formula III is reacted with a heteroaromatic compound of the formula V wherein ring A is a nitrogen containing heterocycle and X is a leaving group, as defined above, which is ortho to a ring nitrogen. The intermediate of the formula IIA that is formed in the foregoing reaction can be further hydrolyzed, under the conditions described above, to yeild the desired final product of formula I. Examples of compounds of the formula V are the following:

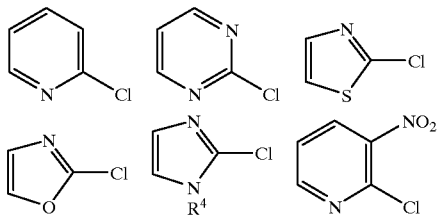

The presence on the above heteroaryl groups of additional EWG's further activates them.

Compounds wherein $R^1$ is another aryl or heteroaryl group can be synthesized in an analogous fashion starting with the appropriate compound of the formula $R^1X$.

Additional compounds of the formula I wherein $R^1$ is substituted aryl or heteroaryl may be obtained from compounds of the formula IIA wherein $R^1$ is a nitroaryl or nitroheteroraryl group, by employing well known synthetic chemical methods. For example, following procedures such as those described by Jerry March, *Advanced Organic Chemistry*, 4th edition pp721–725 and 1216–1217, the nitro group can be reduced to an amine. The newly formed amine can be replaced with other substituents by diazotization and further reaction as summarized in the above reference. For example, compounds of the formula I wherein $R^1$ is an aryl or heteroaryl group substituted with amino, mercapto, halo, cyano, or phenyl can be prepared in this manner.

The starting materials of formula IV and other compounds of the formula $R^1X$ are either commerically available, known in the literature, or readily obtainable from commercially available or known compounds using methods that are known in the art.

The starting materials of the formula III are known in the literature. (See, e.g., European Patent Application 696577A1, referred to above).

Compounds of the formula II wherein one of $R^2$ and $R^3$ is hydrogen can be prepared by partial hydrolysis of the corresponding compounds of formula IIA.

Unless indicated otherwise, the pressure of each of the above reactions is not critical. Generally, the reactions will be conducted at a pressure of about one to about three atmospheres, preferably at ambient pressure (about one atmosphere).

The preparation of other compounds of the formula I not specifically described in the foregoing experimental section can be accomplished using combinations of the reactions described above that will be apparent to those skilled in the art.

The compounds of the formula I that are basic in nature are capable of forming a wide variety of different salts with various inorganic and organic acids. The acid that can be used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

Compounds of the formula that are acidic in nature are capable of forming base salts with various pharmacologically acceptable cations. These salts are all prepared by conventional techniques. The chemical bases that are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the formula I and the pharmaceutically acceptable salts thereof (hereinafter, also referred to, collectively, as "the active compounds of the invention") are useful for the treatment of neurodegenerative, psychotropic and drug or alcohol induced deficits and are potent metabotropic glutamate receptor ligands antagonists. The active compounds of the invention may therefore be used in the treatment or prevention of stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, chemical dependencies and addictions (e.g., addictions to or dependencies on alcohol, opiates, benzodiazepines, nicotine, heroin or cocaine), ocular damage, retinopathy, retinal neuropathy, tinnitus, idiopathic and drug induced Parkinson's Disease, anxiety, emesis, brain edema, chronic and acute pain, tardive dyskinesia and cerebral deficits subsequent to cardiac bypass surgery and grafting.

The following procedure can be used to determine the activity of the therapeutic agents of this invention as agonists and as antagonists of metabotropic glutamate receptors.

Chinese hamster ovary (CHO) cells were transfected with cDNA (mGluR2 and pcDNA3) using a calcium-phosphate method. Positive clones were selected for using geneticin (G418, Gibco, 500–700 μg/ml), and analyzed with RT-PCR for the presence of mGluR2 mRNA (primers for mGluR2: 5'-AAG TGC CCG GAG AAC TTC AAC GAA-3' AND 5'-AAA GCG ACG ACG TTG TTG AGT CCA-3'). Positive clones were grown to confluency and cAMP responses were measured in the presence of 10 μM forskolin. Confluent clones were frozen and stored in liquid nitrogen.

Chinese hamster ovary (CHO) cells stably transfected with the rat metabotropic glutamate receptor, mGluR2, were grown to confluence in Dulbecco's Modified Eagle Medium (DMEM) (Gibco catalog # 11960-044), containing 10% dialysed fetal bovine serum, 1% proline, 0.11 mg/ml sodium pyruvate, 0.5 mg/ml Geneticin, 2 mM I-glutamine, and penicillin/streptomycin. Cells were harvested using a 5 mM ethylenediaminetetraacetic acid (EDTA) solution, and then spun down at 800 rpm in a 4° C. refrigerated centrifuge. The remaining pellet was resuspended in a phosphate-buffered saline solution containing 30 mM HEPES (Giboo, catino.15630-080) 5 mM magnesium chloride ($MgCl_2$), 300 μM 3-Isobutyl-I-methylxanthine (IBMX), and 0.1% dextrose. The cell suspension was added in 200 μl aliquots to flat bottomed polypropylene tubes that were then placed in a 37° C. heated water bath for 22 minutes. If a compound was being tested for antagonist activity, it was allowed to pre-incubate with the cells in the bath during the first 11 minutes. At the end of the 11 minutes, 5 μM forskolin plus a known concentration of an the test compound were added, and the incubation was continued for another 11 minutes. If a compound was being tested for agonist activity, the cells were allowed to shake in the bath for the initial 11 minutes, and then 5 μM forskolin plus a known concentration of agonist were added for the remaining 11 minute incubation. In either case, the reaction was stopped with 25 μl of 6N perchloric acid (PCA), and each tube was transferred immediately to an ice water bath. The pH of each sample was adjusted to approximately 8.0 with the addition of potassium hydroxide (KOH), and stabilized with the addition of Tris, pH 7.4. Aliquots (25 μl) were assayed in a commercial competitive binding kit (Amersham TRK.432). The samples were then harvested onto GF/B filters coated in 0.5% PEI using a 96-well Skatron harvester. Samples were quantified using a 1205 Betaplate liquid scintillation counter.

CPMs from the Betaplate reader were converted to pmoles cAMP/mg protein/minute of incubation with forskolin using an Excel spreadsheet. $EC_{50}$'s and $IC_{50}$'s can be calculated from linear regression of the concentration response data.

The following proceeding can be used to determine the agonist activity of the therapeutic agents of this invention as agonists of metabotropic glutamate receptors.

Chinese hamster ovary (CHO) cells stably transfected with the rat metabotropic glutamate receptor, mGluR2, were grown to confluence in DMEM (Gibco catalog # 11960-044), containing 10% dialyzed fetal bovine serum, 1% proline, 0.11 mg/ml sodium pyruvate, 0.5 mg/ml Geneticin, 2 mM I-glutamine, and penicillin/streptomycin. Cells are harvested using a 5 mM EDTA solution, and homogenized for 10 strokes with a glass-teflon hand held homogenizer, then 50 volumes of a phosphate buffered saline solution (PBS) are added and the solution is spun at 18,000 RPM for 10 minutes at 4° C. The pellet is rehomogenized and resuspended in assay buffer (100 mM HEPES, 1 mM EGTA, pH 7.5) at a concentration that will result in approx. 0.009 mg protein/well. A reaction mix containing 6 mM $MgCl_2$, 0.5 mM adenosine triphosphate (ATP), 0.5 mM 3-isobutyl-1-methylxanthine (IBMX), 0.1 mM guanosine triphosphate (GTP), 10 mM phosphocreatine, 0.31 mg/ml creatine phosphokinase (final concentrations in assay) is prepared just prior to the initiation of the experiment. 20 μl of test compound, 20 μl of forskolin (5 μM final), 20 μl of reaction mix, and 40 μl of tissue are added in consecutive order to a 96-well polypropaline plate. The plate is incubated at 37° C. in a heated water bath for 15 minutes. The reaction is stopped with the addition of 50 μl of 40 mM EDTA. The plate is then transferred to ice and shaken for 10–15 minutes before a 25 μl aliquot is removed for analysis in a commercial competitive binding kit (Amersham TRK.432). After a 2–18 hour incubation in the refrigerator, the samples are harvested onto GF/B filters coated in 0.5% polyethylenimine (PEI) using a 96-well Skatron harvester. Samples were quantified using a 1205 Betaplate liquid scintillation counter.

CPMs from the Betaplate reader are converted to pmoles cAMP/well using an Excel spreadsheet. Agonist compounds are identified by percent reduction of the forskolin signal, also in Excel. $EC_{50}$'s are calculated from linear regression of the concentration response data.

The compositions of the present invention may be formulated in a conventional manner using one or more pharmaceutically acceptable carriers. Thus, the active compounds of the invention may be formulated for oral, buccal, transdermal (e.g., patch), intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use.

Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., stroke) is 0.01 to 50 mg/kg of the active ingredient per unit dose which could be administered, for example, 1 to 4 times per day.

Aerosol formulations for treatment of the conditions referred to above (e.g., stroke) in the average adult human are preferably arranged so that each metered dose or "puff" of aerosol contains 20 mg to 1000 mg of the compound of the invention. The overall daily dose with an aerosol will be within the range 100 mg to 10 mg. Administration may be several times daily, for example 2, 3, 4 or 8 times, giving for example, 1, 2 or 3 doses each time.

The following Examples illustrate the preparation of the compounds of the present invention. Commercial reagents were utilized without further purification. Melting points are uncorrected. All NMR data were recorded at 250, 300 or 400 MHz in deuterochloroform unless otherwise specified and are reported in parts per million (δ) and are referenced to the deuterium lock signal from the sample solvent. All non-aqueous reactions were carried out in dry glassware with dry solvents under an inert atmosphere for convenience and to maximize yields. All reactions were stirred with a magnetic stirring bar unless otherwise stated. Unless otherwise stated, all mass spectra were obtained using chemical impact conditions. Ambient or room temperature refers to 20–25° C. Melting points are uncorrected. HPLC conditions are the following.

(a) Column: Waters Symmetry C18 3.9×150 mm, part no. WAT046980, lot no.T71961R 87

Solvent System: Isocratic 75% 5 mM Ammonium acetate buffer unadjusted/25% Acetonitrile Flow Rate: 0.8 mL/min.

Run Time: 10 min.

Injection Volume: 20 μL

Detection Wavelength: 206.4 nm b) Column: Waters Symmetry C18 4.6×250 mm, part no. WAT054275, lot no. T71141 U 02

Solvent System: Isocratic 5% 5 mM Ammonium acetate buffer unadjusted/95% Acetonitrile Flow Rate: 0.8 mL/min.

Run Time: 10 min.

Injection Volume: 20 μL

Detection Wave length: 203.9 nm c) Column: Waters Spherisorb Phenyl 4.6×250 mm

Solvent System: Isocratic

Flow Rate: 1.0 mL/min.

Run Time: 10 min.

Injection Volume: 15 μL

Detection Wavelength: 203.9 nm

EXAMPLE 1

A. Sodium triacetoxyborohydride (0.0403 g, 0.19 mmol) was added to a mixture of diethyl 2-aminobicyclo[3.1.0] hexane-2,6-dicarboxylate (0.0092 g, 0.038 mmol) and 0.046 mmol of benzaldehyde in dichloromethane (0.92 mL) in a 1.0 mL screw cap vial and the mixture was agitated at ambient temperature overnight. Activity 1 alumina B (50–200 mesh, 0.10 g) was added and the mixture was agitated another 30 min before filtering through activity 1 alumina B (0.5 g). The alumina was washed with 2 mL of 5% methanol/dichloromethane. An aliquot of the filtrate was analyzed by HPLC for unreacted diethyl 2-aminobicyclo [3.1.0]hexane-2,6-dicarboxylate. If this starting material was present, the mixture was not carried on to step 2. The solution was concentrated at 50° C. (19 inches Hg) to give an oily intermediate product.

B. The intermediate product from step 1 was combined with 6 N HCl (0.50 mL) in a 1 mL screw cap vial and agitated at 100° C. overnight. An aliquot was extracted for HPLC analysis. If HPLC analysis indicated that the intermediate product from step 1 was consumed, the reaction was cooled to ambient temperature and applied to strong cation exchange resin (Burdick and Jackson SCX, 0.50 g which had previously been washed with water until the eluant pH was ~4.5). The product was eluted with 2 mL water. Concentration of the eluant at 70° C. (19 inches Hg) gave the off white solid product. The product was characterized by HPLC retention time and mass spectrum parent ion.

The following compounds of the formula I were prepared using an analogous procedure.

[Structure: bicyclic scaffold with R¹(CH₂)ₙ-NH- group, carboxylic acid groups, general formula for the tabulated compounds]

| R¹(CH₂)ₙ | HPLC Retention time, min. (conditions) | Mass Spectra Data |
|---|---|---|
| benzyl (C₆H₅-CH₂) | 1.543 (a) | 276.2 (p + 1) |
| 2-chlorobenzyl | 1.383 (a) | 310.1 (p + 1) |
| 4-chlorobenzyl | 5.302 (c) | 310.4 (p + 1) |
| 3,4-dichlorobenzyl | 6.485 (c) | 344.1 (p + 1) |
| 2-methoxybenzyl | 1.418 (a) | 306.2 (p + 1) |
| 3-methoxybenzyl | 1.450 (a) | 306.3 (p + 1) |
| 4-methoxybenzyl | 5.14 (c) | 306.5 (p + 1) |
| 3-fluorobenzyl | 1.452 (a) | 294.2 (p + 1) |
| 4-fluorobenzyl | 3.858 (b) | 294.2 (p + 1) |
| 2-bromobenzyl | 1.453 (a) | 355.0 (p + 1) |
| 3-bromobenzyl | 5.575 (c) | 354.0 (p + 1) |
| 4-bromobenzyl | 3.908 (b) | 354.0 (p + 1) |
| 2-methylbenzyl | 1.405 (a) | 290.2 (p + 1) |
| 3-methylbenzyl | 1.488 (a) | 290.2 (p + 1) |
| (pyridin-2-yl)methyl | 3.928 (b) | 277.2 (p + 1) |
| (pyridin-3-yl)methyl (R₂) | 3.923 (b) | 277.2 (p + 1) |
| (pyridin-4-yl)methyl | 3.867 (b) | 277.2 (p + 1) |
| (thien-2-yl)methyl | 3.902 (b) | 285.1 (p + 1) |
| (thien-3-yl)methyl | 3.905 (b) | 282.1 (p + 1) |

-continued

| R¹(CH₂)ₙ | HPLC Retention time, min. (conditions) | Mass Spectra Data |
|---|---|---|
| 2-thiazolyl-CH₂ | 1.607 (a) | 283.2 (p + 1) |
| 2-imidazolyl-CH₂ | 3.49 (c) | 266.3 (p + 1) |
| cyclohexyl-CH₂ | 1.445 (a) | 282.2 (p + 1) |
| H₃C-(CH₂)₄-CH₂ | 3.842 (b) | 270.3 (p + 1) |
| (H₃C)₂CH-CH₂ | 3.830 (b) | 256.3 (p + 1) |
| 1-naphthyl-CH₂ | 1.610 (a) | 324.2 (p − 1) |
| 4-phenoxyphenyl-CH₂ | 3.800 (b) | 368.2 (p + 1) |
| 4-(Et₂N)phenyl-CH₂ | 3.862 (b) | 354.2 (p + 1) |
| phenyl-CH₂ | 5.50 (c) | 288 (p − 1) |

What is claimed is:

1. A compound of the formula

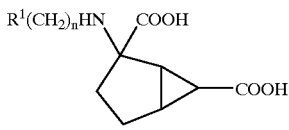

I wherein n is 0–6;

$R^1$ is hydrogen, $(C_1-C_6)$alkyl, or aryl, wherein aryl is selected from phenyl and naphthyl, and wherein said aryl moiety can optionally be substituted with one or more substituents, that are selected, independently, from halo, —SO$(C_1-C_6)$alkyl, —SO$_2R^4$, —SO$_2NR^5R^6$, $(C_1-C^6)$alkyl optionally substituted with from one to seven fluorine atoms, $(C_1-C_6)$alkoxy optionally substituted with from one to seven fluorine atoms, amino, nitro, cyano, carboxy, —CO$_2(C_1-C_6)$alkyl, $(C_1-C_6)$alkylamino, di-amino phenoxy, anilino and phenylthio; $R^4$ is —O$(C_1-C_6)$alkyl, phenyl or $(C_1-C_6)$alkyl; and $R^5$ and $R^6$ are selected, independently, from hydrogen, $(C_1-C_6)$alkyl and phenyl; with the proviso that $R^1$ can not be hydrogen when n is zero or 1; or a pharmaceutically acceptable salt thereof.

2. A compound according to claim 1 wherein $R^1$ is a disubstituted phenyl group having substituents at the meta and para positions.

3. A compound according to claim 1 wherein $R^1$ is a monosubstituted or disubstituted phenyl group wherein one substituent is in the para position.

4. A compound according to claim 1 wherein $R^1(CH_2)_n$ is one of the following groups:

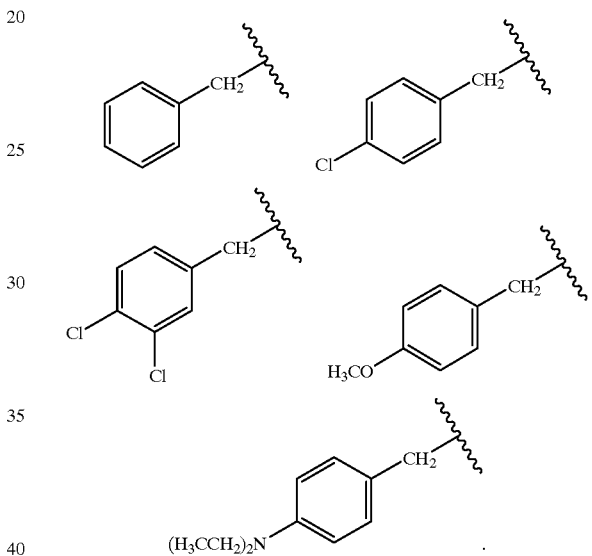

5. A compound according to claim 1 wherein $R^1(CH_2)_n$ is 3-methylbutyl.

6. A compound according to claim 1 wherein $R^1$ is linked to the bicyclic ring of structural formula I via an alkyl group.

7. A compound according to claim 1 wherein said compound is selected from the group consisting of:
2-Benzylamino-bicyclo[3.1.0]hexane-2,6-dicarboxylic acid;
2-(4-Methoxy-benzylamino)-bicyclo[3.1.0]hexane-2,6-dicarboxylic acid;
2-(4-Diethylamino-benzylamino)-bicyclo[3.1.0]hexane-2,6-dicarboxylic acid;
2-(4-Chloro-benzylamino)-bicyclo[3.1.0]hexane-2,6-dicarboxylic acid;
2-(3,4-Dichloro-benzylamino)-bicyclo[3.1.0]hexane-2,6-dicarboxylic acid.

8. A pharmaceutical composition for treating a disorder or condition selected from stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, hypoxia, cardiac arrest, hypoglycemic neuronal damage, chemical dependencies and addictions, ocular damage and retinopathy, idiopathic and drug induced Parkinson's Disease, anxiety, panic disorder, schizophrenia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting in a mammal, comprising an amount of a compound according to claim 1 that is effective in treating such disorder or condition and a pharmaceutically acceptable carrier.

9. A pharmaceutical composition for treating a disorder or condition, the treatment or prevention of which can be effected or facilitated by modulating glutamate neurotransmission in a mammal, comprising an amount of a compound according to claim 1 that is effective in treating such disorder or condition and a pharmaceutically acceptable carrier.

10. A pharmaceutical composition for treating a disorder or condition selected from stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, idiopathic and drug induced Parkinson's Disease, anxiety, panic disorder, schizophrenia, depression, bipolar disorder, obsessive-compulsive disorder, Tourette's syndrome, emesis, brain edema, chronic and acute pain, tardive dyskinesia and cerebral deficits subsequent to cardiac bypass surgery and grafting, in a mammal, comprising a metabotropic glutamate neurotransmission modulating effective amount of a compound according to claim 1 and a pharmaceutically acceptable carrier.

11. A pharmaceutical composition for treating a disorder or condition, the treatment or prevention of which can be effected or facilitated by modulating glutamate neurotransmission in a mammal, comprising a metabotropic glutamate neurotransmission modulating effective amount of a compound according to claim 1 and a pharmaceutically acceptable carrier.

* * * * *